United States Patent
Schweigert

(10) Patent No.: US 6,884,309 B2
(45) Date of Patent: Apr. 26, 2005

(54) COATED MONOFILAMENT TAPE BOBBINS AND METHODS FOR WINDING

(75) Inventor: Michael Schweigert, Stafford, TX (US)

(73) Assignee: International Tape Partners LLC, Stafford, TX (US)

( * ) Notice: Subject to any disclaimer, the term of this patent is extended or adjusted under 35 U.S.C. 154(b) by 273 days.

(21) Appl. No.: 09/935,907

(22) Filed: Aug. 23, 2001

(65) Prior Publication Data

US 2002/0145066 A1 Oct. 10, 2002

Related U.S. Application Data

(60) Provisional application No. 60/263,146, filed on Jan. 22, 2001.

(51) Int. Cl.$^7$ ............................ B65B 81/00; A16C 15/00
(52) U.S. Cl. ......................... 156/172; 156/173; 156/175; 156/169; 156/308.2; 156/309.6; 242/172; 242/173; 132/321
(58) Field of Search ............................ 156/308.2, 309.6, 156/161, 172, 173, 175, 169; 242/172, 173; 132/321

(56) References Cited

U.S. PATENT DOCUMENTS

| | | | |
|---|---|---|---|
| 3,800,812 A | 4/1974 | Jaffe | |
| 4,776,358 A | 10/1988 | Lorch | |
| 4,974,615 A | 12/1990 | Doundoulakis | |
| 5,033,488 A | 7/1991 | Curtis et al. | |
| 5,160,561 A | * 11/1992 | Gruber | 156/175 |
| 5,209,251 A | 5/1993 | Curtis et al. | |
| 5,220,932 A | 6/1993 | Blass | |
| 5,433,226 A | 7/1995 | Burch | |
| 5,479,952 A | 1/1996 | Zachariades et al. | |
| 5,503,842 A | 4/1996 | Fazan et al. | |
| 5,518,012 A | 5/1996 | Dolan et al. | |
| 5,520,351 A | * 5/1996 | Prospero et al. | 242/419.7 |
| RE35,439 E | 2/1997 | Rosenberger | |
| 5,718,251 A | 2/1998 | Gray et al. | |
| 5,755,243 A | 5/1998 | Roberts et al. | |
| 5,760,117 A | 6/1998 | Chen | |
| 5,765,576 A | 6/1998 | Dolan et al. | |
| 5,787,758 A | 8/1998 | Sheldon | |
| 5,845,652 A | 12/1998 | Tseng et al. | |
| 5,848,600 A | 12/1998 | Bacino et al. | |
| 5,884,639 A | 3/1999 | Chen | |
| 5,911,228 A | 6/1999 | Curtis et al. | |
| 5,918,609 A | 7/1999 | Tsao et al. | |
| 5,962,572 A | 10/1999 | Chen | |
| 5,998,431 A | 12/1999 | Tseng et al. | |
| 6,003,525 A | 12/1999 | Katz | |
| 6,027,592 A | 2/2000 | Tseng et al. | |
| 6,083,208 A | 7/2000 | Modak et al. | |
| 6,148,830 A | 11/2000 | Chen | |
| 6,161,555 A | 12/2000 | Chen | |

FOREIGN PATENT DOCUMENTS

| | | | |
|---|---|---|---|
| GB | 328944 A | * | 5/1930 |
| GB | 940342 A | * | 10/1963 |

* cited by examiner

Primary Examiner—Jeff H. Aftergut

(57) ABSTRACT

Bobbin wound coated monofilament tapes where the coating comprises between 20% and 120% by weight of said tape, and the process for bobbin winding coated monofilament dental tapes comprising combining a coating conditioning means with means for winding at substantially constant tensions to produce controlled tension bobbins that do not unwind, that dispense uniformly free from back lashing, and that are substantially free from coating displacement and winding displacement when exposed to high temperatures and high relative humidity and that have tack values from between about 0.1 and about 0.5 grams.

8 Claims, 10 Drawing Sheets

COATED MONOFILAMENT TAPE BOBBINS AND METHODS FOR WINDING

CROSS-REFERENCE TO RELATED APPLICATIONS

This application claims priority from copending Provisional Patent Application Ser. No. 60/263,146, filed Jan. 22, 2001, the disclosure of which is hereby incorporated herein by reference.

BACKGROUND OF THE INVENTION

Various monofilament dental tapes, as distinguished from multifilaments tapes, have been commercialized which feature reduced shredding, a primary consumer complaint registered for most multifilament dental flosses. These are described and claimed in U.S. Pat. Nos. Re 35,439; 3,800,812; 4,974,615; 5,760,117; 5,433,226; 5,479,952; 5,503,842; 5,755,243; 5,845,652; 5,884,639; 5,918,609; 5,962,572; 5,998,431; 6,003,525; 6,083,208; 6,148,830; 6,161,555; and 6,027,592, the disclosures of which are hereby incorporated herein by reference. These dental tapes generally have serious shortcomings in gentleness, in delivering coatings during flossing and in being handled easily and conveniently during flossing Polytetrafluoroethylene (PTFE) based interproximal devices are described in: U.S. Pat. Nos. 5,209,251; 5,033,488; 5,518,012; 5,911,228; 5,220,932; 4,776,358; 5,718,251; 5,848,600; 5,787,758; and 5,765,576, which are hereby incorporated herein by reference. To date, no commercial versions of these tapes have been coated effectively and cannot be used to deliver active ingredients, interproximally and subgingivally during flossing. Handling during flossing, i.e., wrapping the tape around fingers in preparation for flossing, is difficult. Most fail to provide a gentle tape edge. Many tapes are plagued with serious dimensional inconsistency problems, as well.

See also co-pending patent application Ser. Nos. 60/227,196; 60/227,239; 60/227,240; 60/227,246; 60/227,244; 60/227,255; and 60/227,433; all of which are hereby incorporated by reference.

Coated monofilament dental tapes including: elastomeric, polytetrafluoroethylene (PTFE), bicomponent and other polymeric tapes coated with ingredients at relatively high levels (between about 20% and 120% by weight of the tape) and increasing by between about 50% and 150% the thickness of the tape after coating are described in the various referenced co-pending applications cited herein. Generally, these coatings are applied to both sides of the monofilament tape. These coated monofilament dental tapes feature an enhanced flossing performance attributed primarily to the various saliva soluble coatings applied to the various monofilament dental tapes. Total delivery of a wide range of active ingredients contained in the coatings into the oral cavity during flossing is a key performance feature of these saliva soluble coated monofilament tapes.

Traditionally, most commercial dental tapes are dispensed in about 18-inch increments from a dispenser package that contains from between about 8 yds. and about 200 yds. of tape wound onto a bobbin means. For promotion purposes, samples of dental tapes are generally distributed in single dose packages containing one or two pieces of tape of about 18 inches each. Heretofore, uncoated or lightly waxed dental tape dispenser packages have been manufactured using traditional "yarn" bobbin winding means. That is, high speed bobbin winding machines have been adapted from yarn and thread manufacturing operations to wind uncoated or lightly waxed dental tapes suitable for use in traditional dental tape dispensers utilizing methods commonly known in the art for winding waxed or unwaxed multifilament and monofilament dental flosses.

Coated elastomeric and other forms of monofilament dental tapes such as described in the various co-pending applications and issued U.S. Patents cited above have proven to be most difficult to bobbin wind on cores using traditional bobbin winding equipment and procedures. That is, unlike uncoated or lightly waxed tapes, these rather heavily coated monofilament tapes tend to slip off the bobbin during winding, and generally resist buildup to a bobbin of the required yardage. Further, when traditional heat sources are applied to the tape prior to the tape's arrival on the bobbin to "tack" one wind of the tape to previously wound coated tape "winds", the winding tension tends to increase dramatically as the diameter of the wound bobbin increases. This increased tension on the wound bobbin, as it builds, coupled with the near melt heating conditions imposed on the coated monofilament tape coating up-stream from the bobbin core tends to deform the bobbins further. Subsequent exposure of bobbins to high temperature and/or high relative humidity tends to displace the coating and/or deform the bobbin.

Typical bobbin deformations resulting from this increased winding tension with improper conditioning and location of the "tacking" energy input and/or from exposure to high temperature and high humidity includes bobbins which can be described as "out-of-round", "squashed bobbins", "bulging bobbins", "bobbins with displaced coatings squeezed out of the bobbins", etc. Obviously, such misshapen, deformed and coating displaced bobbins do not dispense effectively in the various commercial tape dispensers available, most of which call for commercial bobbins within certain fairly close dimensional specifications including diameter, width, straight sides, etc. The net is, elastomeric monofilament dental tapes, monofilament PTFE dental tapes, bicomponent tapes and other monofilament polymeric monofilament dental tapes with coatings from between about 20% and about 120% by weight of the monofilament tape, when commercially bobbin wound using conventional thread, yarn and/or dental floss/tape bobbin winding processes and equipment, can produce deformed bobbins that are out-of-spec for use with most commercial tape dispensers and/or bobbins that deform and/or release that coating when exposed to high temperature and/or high relative humidity.

In addition, these coated monofilament tape bobbins tend to deform when exposed to elevated temperatures and/or high relative humidity.

SUMMARY OF THE INVENTION

This invention relates to bobbin winding coated monofilament dental tapes having a wide range of coating levels, using a coating conditioning means in conjunction with a coated monofilament tape tension controlling means to produce substantially round bobbins with the coated tape secured to the bobbin, such that it is dispensed uniformly free from unwinding, backlash, bobbin deformation, with a tack value from between 0.1 and about 0.5 grams.

One embodiment of the present invention is to provide a method for bobbin winding coated monofilament dental tapes at commercial speeds without bobbin deformation.

Another embodiment of the present invention is to provide a method for bobbin winding coated monofilament dental tapes having a wide range of coating levels at commercial speeds without bobbin deformation.

A further embodiment of the present invention is to provide a means for bobbin winding coated monofilament dental tapes constructed of various polymeric materials, wherein these coated tapes, once bobbin wound, can be dispensed consistently from commercial tape dispensers when exposed to elevated temperatures and high relative humidity.

Yet another embodiment of the present invention is to provide a means for bobbin winding coated elastomeric monofilament dental tapes at commercial speeds free from bobbin deformation where all revolutions (wraps) of the coated elastomeric monofilament tape are secure to the bobbin and such bobbins continue to hold their shape and retain their coatings when exposed to elevated temperature and/or high relative humidity.

Still another embodiment of the present invention is to provide a means for bobbin winding coated monofilament PTFE dental tapes with coatings of between 20% and 120% by weight of the PTFE at commercial speeds free from bobbin deformation and where all revolutions (wraps) of the coated monofilament PTFE tape are held secure to the bobbin and such bobbins continue to hold their shape and retain their coatings when exposed to elevated temperature and/or high relative humidity.

Another embodiment of the present invention is to provide a means for bobbin winding coated bicomponent dental tapes with coatings between 20% and 120% by weight of the bicomponent tape at commercial speeds free from bobbin deformation and where all revolutions (wraps) of the coated bicomponent tape are held secure to the bobbin and such bobbins continue to hold their shape and retain their coatings when exposed to elevated temperature and/or high relative humidity.

Another embodiment of the present invention is to provide a means for bobbin winding coated monofilament dental tapes of polymeric construction with coatings of between 20% and 120% by weight of the polymeric tape at commercial speeds free from bobbin deformation and where all revolutions (wraps) of the coated monofilament tape are held secure to the bobbin and such bobbins continue to hold their shape and retain their coatings when exposed to elevated temperature and/or high relative humidity.

Yet another embodiment of the present invention is to provide a uniformly wound bobbin of coated monofilament tape that is free from: (a) deformation, (b) premature release of revolutions of the wound tape, and (c) excessive winding tension wherein, upon unwinding, the coated tape releases from the bobbin evenly without disrupting said coating with minimal drag, and substantially free from backlashes and where the coated monofilament tape retains its shape and coating when exposed to elevated temperatures and high relative humidity.

Still another embodiment of the present invention is to provide wound bobbins of coated monofilament tape where some of the coating is conditioned such that said coating adheres to the surface of the previous winds of bobbin wound coated monofilament tape and provides a tack value up to about 0.5 grams.

Another embodiment of the present invention is to provide bobbin wound coated monofilament tape that unwinds evenly free from backlashes with a tack value between about 0.1 and about 0.5 grams.

DETAILED DESCRIPTION OF THE PREFERRED EMBODIMENTS

Specifically, the present invention relates to bobbins of coated monofilament tape and to an improved means for bobbin winding a broad range of coated monofilament tapes, including coated elastomeric and PTFE tapes, as well as coated bicomponent and other monofilament polymeric dental tapes, wherein said coated monofilament tape is subjected to conditioning means, whereby the coating on said monofilament tape is conditioned to adhere to previous winds on the bobbin and the tension on this conditioned coated monofilament tape is controlled during winding to avoid bobbin deformation during bobbin winding and/or coating displacement and to provide bobbins free from deformation and coating displacement when exposed to elevated temperatures and/or elevated relative humidity.

The coating conditioning means is preferably a physical energy means such as heating, but can be a chemical means, whereby the coating is "tackified" chemically. The conditioning means and winding tension provides tack values for the bobbins of the present invention from between about 0.2 and 0.4 grams.

In a preferred embodiment, the bobbin winding invention includes coating conditioning whereby:

a "temperature conditioning" means is provided prior to wrapping on a bobbin, in combination with:

variable, controlled speed bobbin winding means, thereby minimizing the tension applied to the bobbin as the temperature conditioned coated tape is wound onto the bobbin.

Under some winding conditions, it may be desirable to direct additional energy to the appropriate area of the bobbin utilizing various sources of controllable, "directable energy" such as: hot air, radiant heat, lasers, radio frequency and the like to supplement the coating conditioning.

The present invention provides bobbins of coated monofilament tape having various levels of coating wherein:

the coated monofilament tape remains intact on the bobbin with a minimum of tension, the bobbin remains substantially dimensionally uniform with substantially no coating displacement, and the coated monofilament tape is consistently releasable from the bobbin during dispensing with a minimum of drag having a tack value between about 0.1 and about 0.5 grams, and where said bobbin is substantially free from winds falling off the bobbin and is substantially free form "back lashing" and/or coating displacement when exposed to elevated temperatures and/or elevated relative humidity.

The preferred coating conditioning means of the present invention comprises one or more of the following (see details in FIGS. 1, 1a, 1b, 1c and 2.):

a controlled "temperature conditioning" means over, through or on a ceramic eyelet which the tape traverses prior to being wound onto a bobbin, a directable source of energy which is targeted onto the bobbin during winding and/or a controlled temperature ceramic eyelet that contacts the bobbin during winding.

Figure 3:
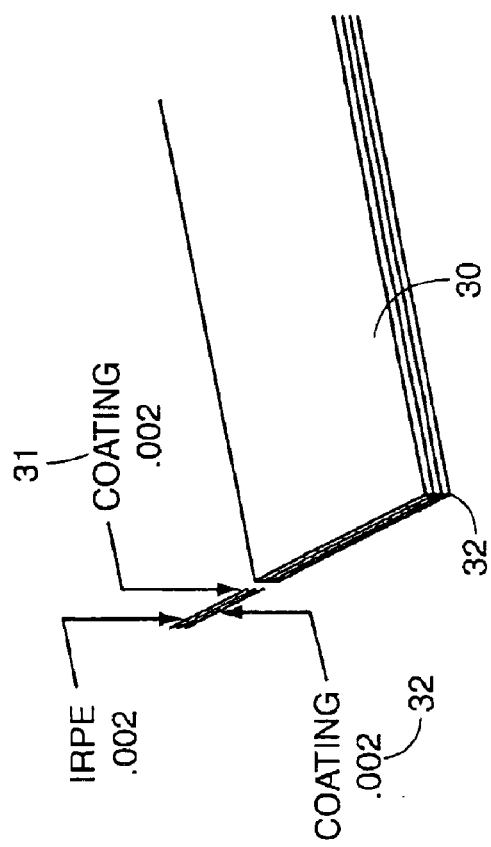
FIG. 3 is a schematic drawing illustrating the coated tape as it is dispensed from a dispenser showing the coating on both sides of the tape.

This "heat tacking" coating conditioning embodiment of the present invention is illustrated in more detail in FIGS. 1, 1a, 1b, 1c and 2 of the drawings. The coated tape is illustrated in FIG. 3.

The various monofilament tapes described in the U.S. Patents referenced above can be coated with from 20% to 120% by weight of the coatings described in Table 5 below. These coated tapes can be bobbin wound according to the present invention. Particularly preferred coated monofilament tapes suitable for bobbin winding according to the present invention are described in Tables 1 to 4 below:

TABLE 1

TAPE COMPOSITION

| Ex. No. | Thermoplastic Elastomer Type | Manufacturer | Trade name | Grade | Silicone Process Aid (%) | TiO$_2$ (%) | Secondary Polymer added Type (%) | Other Add'n Type (%) |
|---|---|---|---|---|---|---|---|---|
| 2 | PEBA polyester amide | Atofina | PEBAX | 55/33 | 3.5 | 1.8 | PP - 4.7 | — |
| 3 | PEBA polyester amide | " | " | " | 3.5 | 1.8 | PP - 4.7 Adflex - 5 | — |
| 4 | PEBA polyester amide | " | " | " | 3.5 | 1.8 | PP - 9.7 | — |
| 5 | PEBA polyester amide | Atofina | PEBAX | 63/33 | 0 | 0 | 0 | — |
| 6 | PEBA polyester amide | " | " | " | 0 | 1.8 | PP - 1.2 | — |
| 7 | PEBA polyester amide | " | " | " | 3.5 | 1.8 | PP - 4.7 | — |
| 8 | PEBA polyester amide | " | " | " | 3.5 | 1.8 | PP - 4.7 Adflex - 5 | — |
| 9 | PEBA polyester amide | " | " | " | 3.5 | 1.8 | PP - 9.7 | — |
| 10 | PEBA polyester amide | " | " | " | 3.5 | 1.8 | PP - 4.7 Nylon 11 - 5 | — |
| 11 | TPE polyether ester | DuPont | Hytrel | 6359FG | 2.3 | 1.0 | 0 | Ca Stearate 0.1 |
| 12 | TPE polyether ester | " | " | " | 3.5 | 1.8 | PP - 4.7 | Ca Stearate 0.1 |
| 13 | TPE-E polyether ester | DSM | Arnitel | PM581 | 0 | 0 | 0 | — |
| 14 | TPE-E polyether ester | " | " | " | 0 | 1.8 | PP - 1.2 | — |
| 15 | TPE-E polyether ester | " | " | " | 3 | 0 | PBT - 5 | — |
| 16 | TPE-E polyether ester | " | " | " | 0 | 0 | PBT - 5 | — |
| 17 | TPE-E polyether ester | " | " | " | 0 | 1.8 | PP - 1.2 PBT - 5 | — |

| | PROCESSING CONDITIONS | | | PROPERTIES | | DIMENSIONS | | | UTILITY FACTORS | | |
|---|---|---|---|---|---|---|---|---|---|---|---|
| Ex. No. | Melt Temp °C. | Draw Temp °C. | Draw Ratio | Break Strength in Newtons | Elongation to Break (%) | Elastic Limit (%) | Decitex | Width (mm) | Thick (mm) | Gentleness Perception | Tape Flex Twist Index | Hardness Shore D |
| 2 | 260 | 130 | 6.8:1 | 30 | 26 | 0 | 750 | 1.30 | 0.063 | 6 | 4 | 37 |
| 3 | 260 | 130 | 6.5:1 | 27 | 18 | 0 | 760 | 1.30 | 0.063 | 6 | 4 | 37 |
| 4 | 260 | 130 | 6.8:1 | 26 | 19 | 0 | 760 | 1.30 | 0.063 | 6 | 4 | 37 |
| 5 | 260 | 135 | 6:1 | 30 | 15 | 0 | 805 | 1.44 | 0.065 | 5.5 | 4 | 36 |
| 6 | 260 | 135 | 6.3:1 | 32.36 | 13 | 0 | 800 | 1.41 | 0.067 | 5.5 | 4 | 36 |
| 7 | 260 | 135 | 6.2:1 | 33.47 | 17 | 0 | 860 | 1.36 | 0.066 | 5.5 | 4 | 36 |
| 8 | 260 | 135 | 6.2:1 | 25.94 | 14 | 0 | 810 | 1.32 | 0.078 | 5.5 | 4 | 36 |
| 9 | 260 | 135 | 6.2:1 | 29.46 | 14 | 0 | 780 | 1.34 | 0.069 | 5.5 | 4 | 36 |
| 10 | 260 | 135 | 6.2:1 | 30.63 | 13 | 0 | 810 | 1.30 | 0.065 | 5.5 | 4 | 36 |
| 11 | 225 | 130 | 5:1 | 20 | 20 | 15 | 1400 | 1.70 | 0.070 | 7 | 3 | 33 |
| 12 | 225 | 140 | 5.7:1 | 24 | 14 | 10 | 1230 | 1.70 | 0.070 | 7 | 3 | 33 |
| 13 | 235 | 140 | 4.3:1 | 18 | 13 | 10 | 1500 | 1.63 | 0.084 | 7 | 3 | 33 |
| 14 | 240 | 115 | 4.3:1 | 19 | 14 | 5 | 1634 | 1.64 | 0.085 | 7 | 3 | 33 |
| 15 | 235 | 140 | 4.3:1 | 19 | 10 | 3 | 1580 | 1.68 | 0.079 | 7 | 3 | 33 |
| 16 | 235 | 140 | 4.3:1 | 18 | 12 | 2 | 1500 | 1.70 | 0.086 | 7 | 3 | 33 |
| 17 | 235 | 140 | 4.3:1 | 21 | 15 | 4 | 1575 | 1.77 | 0.083 | 7 | 3 | 33 |

TABLE 2

| | TAPE COMPOSITION | | | | | | | |
|---|---|---|---|---|---|---|---|---|
| Ex. No. | Thermoplastic Elastomer Type | Manufacturer | Trade name | Grade | Silicone Process Aid (%) | TiO₂ (%) | Secondary Polymer added Type (%) | Other Add'n Type (%) |
| 18 | TPE-E polyether ester | DSM | Arnitel | EM550 | 0 | 0 | 0 | — |
| 19 | TPE-E polyether ester | " | " | " | 0 | 1.8 | PP - 1.2 | — |
| 20 | TPE-E polyether ester | " | " | " | 0 | 1.8 | PP - 6.2 | — |
| 21 | TPE-E polyether ester | " | " | " | 0 | 0 | PBT - 5 | — |
| 22 | TPE-P polyether ester | OSM | Arnitel | EM630 | 0 | 0 | 0 | — |
| 23 | TPE-P polyether ester | " | " | " | 0 | 1.8 | PP - 1.2 | — |
| 24 | TPE-P polyether ester | " | " | " | 0 | 1.8 | PP - 1.2 Adflex - 5 | — |
| 25 | TPE-P polyether ester | " | " | " | 0 | 1.8 | PP - 6.2 | — |
| 26 | TPE-P polyether ester | " | " | " | 0 | 0 | PBT - 5 | — |
| 27 | TPE-P polyester ester | DSM | Arnitel | UM552 | 0 | 0 | 0 | — |
| 28 | TPE-P polyester ester | " | " | " | 0 | 0 | 0 | Ca Stearate 0.1 |
| 29 | TPE-P polyester ester | " | " | " | 0 | 1.8 | PP - 1.2 | — |
| 30 | TPE-P polyester ester | " | " | " | 0 | 0 | Adflex - 5 | — |
| 31 | TPE-P polyester ester | " | " | " | 0 | 1.5 | PP - 1.2 PBT - 5 | Ca Stearate 0.1 |
| 32 | TPE-P polyester ester | " | " | " | 0 | 0 | PBT - 5 | Ca Stearate 0.1 |
| 33 | EPDM TPV | Monteil | Adflex | Q100F | 0 | 0 | PP - 20 | — |
| 34 | EPDM TPV | " | " | " | 3.5 | 1.8 | PP - 24.7 | — |
| 35 | EPDM TPV | " | " | " | 7 | 3 | PP - 30 | — |
| 36 | EPDM TPV | " | " | " | 7 | 3 | PP - 34.7 | — |
| 37 | EPDM TPV | " | " | " | 7 | 3 | PP - 40 | — |

| | PROCESSING CONDITIONS | | | PROPERTIES | | DIMENSIONS | | | UTILITY FACTORS | | |
|---|---|---|---|---|---|---|---|---|---|---|---|
| Ex. No. | Melt Temp °C. | Draw Temp °C. | Draw Ratio | Break Strength in Newtons | Elongation to Break (%) | Elastic Limit (%) | Decitex | Width (mm) | Thickness (mm) | Gentleness Perception | Tape Flex-Twist Index | Hardness Shore D |
| 18 | 240 | 140 | 4.3:1 | 23 | 25 | 7 | 1800 | 1.95 | 0.096 | 7 | 3 | 33 |
| 19 | 240 | 115 | 6:1 | 27 | 11 | 5 | 1050 | 1.47 | 0.071 | 7 | 3 | 33 |
| 20 | 240 | 140 | 5.6:1 | 26 | 17 | 5 | 1216 | 1.45 | 0.071 | 7 | 3 | 33 |
| 21 | 240 | 145 | 5.9:1 | 28 | 145 | 5 | 1220 | 1.55 | 0.074 | 7 | 3 | 33 |
| 22 | 235 | 150 | 4.5:1 | 18 | 12 | 4 | 1090 | 1.44 | 0.067 | 7 | 3 | 33 |
| 23 | 235 | 150 | 4.7:1 | 17 | 11 | 4 | 1130 | 1.50 | 0.068 | 7 | 3 | 33 |
| 24 | 235 | 150 | 4.6:1 | 18 | 10 | 7 | 961 | 1.35 | 0.065 | 7 | 3 | 33 |
| 25 | 235 | 150 | 4.6:1 | 14 | 30 | 10 | 965 | 1.24 | 0.073 | 7 | 3 | 33 |
| 26 | 235 | 150 | 4.6:1 | 20 | 12 | 5 | 1018 | 1.39 | 0.069 | 7 | 3 | 33 |
| 27 | 240 | 150 | 6.6:1 | 32 | 12 | 8 | 1300 | 1.49 | 0.070 | 7.5 | 3.5 | 31 |
| 28 | 230 | 150 | 5.6:1 | 26 | 15 | 8 | 1090 | 1.40 | 0.070 | 7.5 | 3.5 | 31 |
| 29 | 240 | 150 | 6.3:1 | 29 | 16 | 8 | 1150 | 1.46 | 0.070 | 7.5 | 3.5 | 31 |
| 30 | 230 | 140 | 5.6:1 | 30 | 16 | 10 | 1233 | 1.48 | 0.069 | 7.5 | 3.5 | 31 |
| 31 | 230 | 145 | 5.7:1 | 22 | 19 | 10 | 1108 | 1.53 | 0.067 | 7.5 | 3.5 | 31 |
| 32 | 230 | 245 | 5.3:1 | 24 | 14 | 8 | 1143 | 1.48 | 0.064 | 7.5 | 3.5 | 31 |
| 33 | 240 | 130 | 4.5:1 | 26 | 20 | 0 | 910 | 1.60 | 0.064 | 5.5 | NT | NT |
| 34 | 240 | 130 | 4.5:1 | 25 | 24 | 0 | 940 | 1.59 | 0.064 | 5.5 | NT | NT |
| 35 | 240 | 130 | 4.7:1 | 28 | 20 | 0 | 870 | 1.58 | 0.064 | 5.5 | NT | NT |
| 36 | 240 | 130 | 4.7:1 | 27 | 23 | 0 | 880 | 1.58 | 0.060 | 5.5 | NT | NT |
| 37 | 240 | 130 | 4.7:1 | 35 | 18 | 0 | 720 | 1.44 | 0.063 | 5 | NT | NT |

TABLE 3

TAPE COMPOSITION

| Ex. No. | Thermoplastic Elastomer Type | Manufacturer | Trade name | Grade | Silicone Process Aid (%) | TiO$_2$ (%) | Secondary Polymer added Type (%) | Other Add'n Type (%) |
|---|---|---|---|---|---|---|---|---|
| 38 | PEBA polyester amide | Atofina | PEBAX | 55133 | 0 | 1.8 | PP - 1.2 | — |
| 39 | PEBA polyester amide | " | " | " | 3.5 | 1.8 | PP - 4.7 EMA - 3 | — |
| 40 | PEBA polyester amide | " | " | " | 3.5 | 1.8 | PP - 4.7 | — |
| 41 | PEBA | Atofina | PEBAX | 63/33 | 3.5 | 1.8 | PP - 4.7 EMA - 3 | — |
| 42 | PEBA | Atofina | PEBAX | 63/33 | 0 | 0 | Nylon 11 - 5 | PDVF - 3 |
| 43 | TPE-E polyether ester | DSM | Arnitel | PM581 | 3 | 0 | 0 | — |
| 44 | TPE-E polyether ester | DSM | Arnitel | EM550 | 3 | 0 | 0 | — |
| 45 | TPE-E polyether ester | " | " | " | 3 | 1.8 | PP - 1.2 EMA - 3 | — |
| 46 | TPE-E polyether ester | DSM | Arnitel | UM552 | 3 | 1.8 | PP - 1.2 | — |

| | PROCESSING CONDITIONS | | | PROPERTIES | | DIMENSIONS | | | UTILITY FACTORS | | | |
|---|---|---|---|---|---|---|---|---|---|---|---|---|
| Ex. No. | Melt Temp °C. | Draw Temp °C. | Draw Ratio | Break Strength in Newtons | Elongation to Break (%) | Elastic Limit (%) | Decitex | Width (mm) | Thickness (mm) | Gentleness Perception | Tape Flex Twist Index | Hardness Shore D |
| 38 | 260 | 130 | 6.8:1 | 28 | 24 | 0 | 775 | 1.30 | 0.063 | 6 | 4 | 37 |
| 39 | 260 | 130 | 7:1 | 28 | 30 | 3 | 750 | 1.30 | 0.063 | 8 | 4 | 37 |
| 40 | 260 | 130 | 6.8:1 | 29 | 24 | 0 | 800 | 1.35 | 0.070 | 6 | 4 | 37 |
| 41 | 260 | 135 | 6.5:1 | 31 | 20 | 3 | 800 | 1.40 | 0.065 | 5.5 | 4 | 36 |
| 42 | 260 | 135 | 6.2:1 | 28 | 14 | 0 | 800 | 1.30 | 0.065 | 5.5 | 4 | 36 |
| 43 | 235 | 140 | 5:1 | 22 | 16 | 7 | 1400 | 1.60 | 0.079 | 7 | 3 | 33 |
| 44 | 240 | 140 | 6:1 | 25 | 20 | 7 | 800 | 1.30 | 0.060 | 7 | 3 | 33 |
| 45 | 240 | 140 | 6:1 | 27 | 15 | 5 | 850 | 1.35 | 0.065 | 7 | 3 | 33 |
| 46 | 240 | 150 | 6:1 | 27 | 17 | 10 | 1100 | 1.47 | 0.069 | 7.5 | 3 | 33 |

TABLE 4

TAPE COMPOSITION

| Ex. No. | Thermoplastic Elastomer Type | Manufacturer | Trade name | Grade | Silicone Process Aid (%) | TiO$_2$ (%) | Secondary Polymer added Type (%) | Other Add'n Type (%) |
|---|---|---|---|---|---|---|---|---|
| 47 | Styrenics SEBS | Alphagary | Evoprene | G978 | 0 | 1.8 | PP - 1.2 | — |
| 48 | Styrenics SEBS | " | " | " | 3 | 1.8 | PP - 1.2 | — |
| 49 | Styrenics SEBS | " | " | " | 0 | 1.8 | PP - 1.2 EMA - 3 | — |
| 50 | Styrenics SEBS | " | " | " | 3.5 | 1.8 | PP - 9.7 | — |
| 51 | Styrenics SEBS | " | " | " | 3.5 | 1.8 | PP - 9.7 PS - 5 | — |
| 52 | TPU | Dow | Pelethane | 2103-90AEN | 0 | 1.8 | PP - 1.2 | — |
| 53 | TPU | " | " | 90AEN | 3 | 1.8 | PP - 1.2 | — |
| 54 | TPU | " | " | 90AEN | 0 | 1.8 | PP - 1.2 EMA - 3 | — |
| 55 | TPU | " | " | 90AEN | 3.5 | 1.8 | PP - 9.7 | — |
| 56 | TPV | DSM | Sarlink | 4149D | 0 | 1.8 | PP - 1.2 | — |
| 57 | " | " | " | " | 3 | 1.8 | PP - 1.2 | — |
| 58 | " | " | " | " | 0 | 1.8 | PP- 1.2 EMA - 3 | — |
| 59 | " | " | " | " | 3 | 1.8 | PP - 6.2 | — |

TABLE 4-continued

| | PROCESSING CONDITIONS | | | PROPERTIES | | DIMENSIONS | | | UTILITY FACTORS | | | |
|---|---|---|---|---|---|---|---|---|---|---|---|---|
| Ex. No. | Melt Temp ° C. | Draw Temp ° C. | Draw Ratio | Break Strength in Newtons | Elongation to Break (%) | Elastic Limit (%) | Decitex | Width (mm) | Thickness (mm) | Gentleness Perception | Tape Flex Twist Index | Hardness Shore D |
| 47 | 200 | 100 | 7:1 | 19 | 30 | 10 | 1100 | 1.30 | 0.060 | 6 | 4 | 37 |
| 48 | 200 | 100 | 7:1 | 20 | 35 | 12 | 1100 | 1.30 | 0.060 | 6 | 4 | 37 |
| 49 | 200 | 100 | 7.2:1 | 17 | 32 | 12 | 1100 | 1.30 | 0.060 | 6 | 4 | 37 |
| 50 | 200 | 100 | 7:1 | 14 | 20 | 7 | 1100 | 1.30 | 0.060 | 8 | 4 | 37 |
| 51 | 200 | 100 | 7:1 | 22 | 28 | 8 | 1100 | 1.30 | 0.060 | 6 | 4 | 37 |
| 52 | 230 | 120 | 7:1 | 32 | 15 | 5 | 1200 | 1.40 | 0.068 | 7 | 3 | 33 |
| 53 | 230 | 120 | 6:1 | 30 | 17 | 6 | 1200 | 1.40 | 0.068 | 7 | 3 | 33 |
| 54 | 230 | 120 | 6:1 | 26 | 16 | 6 | 1200 | 1.40 | 0.068 | 7 | 3 | 33 |
| 55 | 230 | 120 | 5:1 | 22 | 10 | 2 | 1300 | 1.45 | 0.070 | 7 | 3 | 33 |
| 56 | 220 | 105 | 4.5:1 | 20 | 20 | 5 | 1400 | 1.45 | 0.072 | 6 | 4 | 37 |
| 57 | 220 | 105 | 5:1 | 22 | 35 | 7 | 1300 | 1.40 | 0.070 | 6 | 4 | 37 |
| 58 | 220 | 105 | 4.8:1 | 19 | 20 | 5 | 1350 | 1.48 | 0.075 | 6 | 4 | 37 |
| 59 | 220 | 105 | 4.2:1 | 15 | 20 | 5 | 1450 | 1.48 | 0.075 | 6 | 4 | 37 |

Figure 1A:
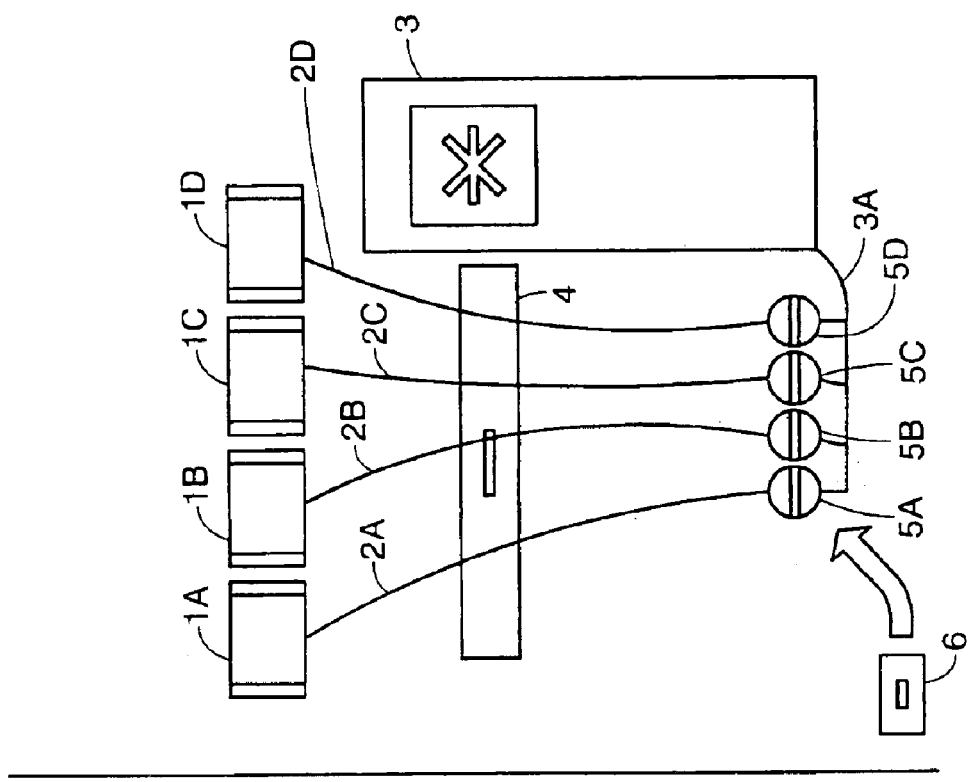
FIG. 1, comprised of FIGS. 1A, 1B and 1C, are schematic drawings of the bobbin winding process and apparatus of the present invention.

Referring to FIG. 1, FIG. 1a is a general schematic drawing of the bobbin winding process of the present invention. King spools of coated monofilament dental tape, designated 1a through 1d, supply coated tapes, designated 2a through 2d, to tension controlled bobbin winders, designated as 5a through 5d. The take up tension on bobbin winders, 5a through 5d, is controlled by programmable logic controller means, 3, through connecting means, 3a, resulting in controlled tension during winding.

Coated monofilament tapes, 2a through 2d, are passed over or through a coating conditioning means, 4, prior to being wound by bobbin winders, 5a through 5d. During bobbin winding, bobbin winders, 5a through 5d, are exposed to a suitable directed energy source, 6, such as hot air, radiant heat, lasers, radio frequency, contact heat, etc., for completion of the heat tacking process. Bobbins wound under these conditions are dimensionally stable, retain the coatings and have tack values between about 0.1 and about 0.5 grams.

Figure 1B:
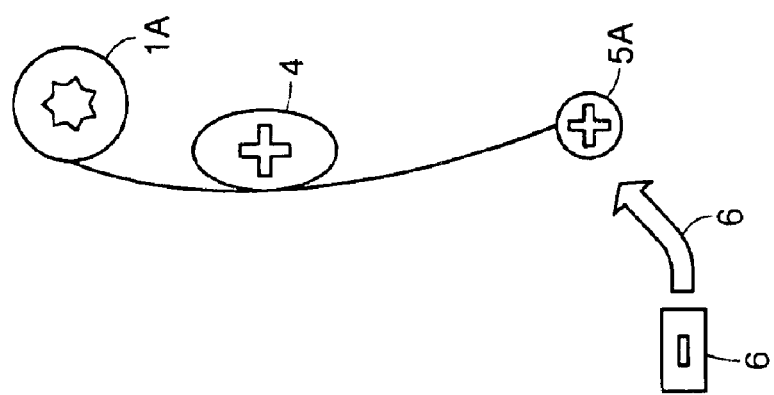

FIG. 1b is a side-profile schematic view of bobbin winding means, 5a, with coated monofilament tape, 2a, engaging both the temperature conditioning and coating conditioning means, 4, and directed energy source, 6.

Figure 1C:
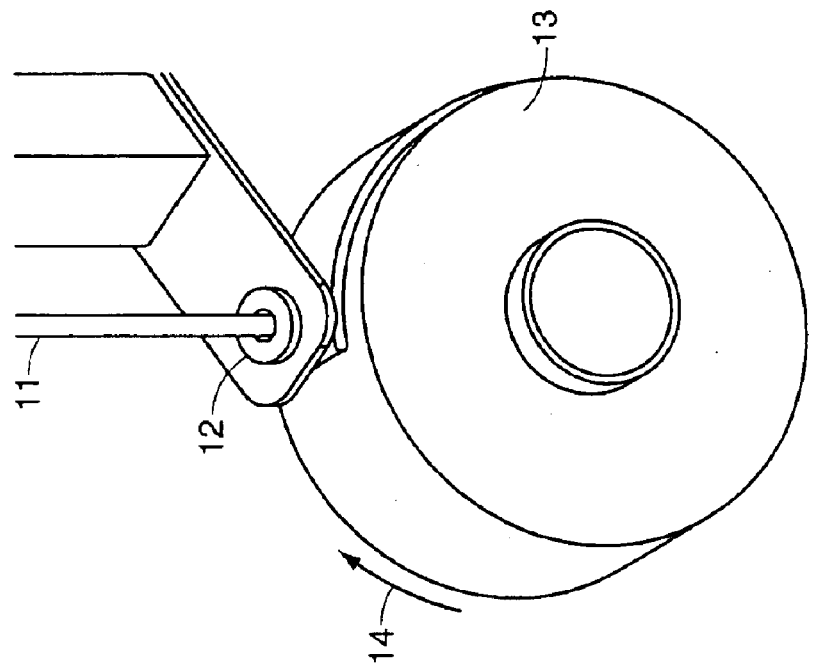

FIG. 1c illustrates coated monofilament tape, 11, passing through heated coating conditioning means, 12, prior to winding onto bobbin, 13.

Figure 2:
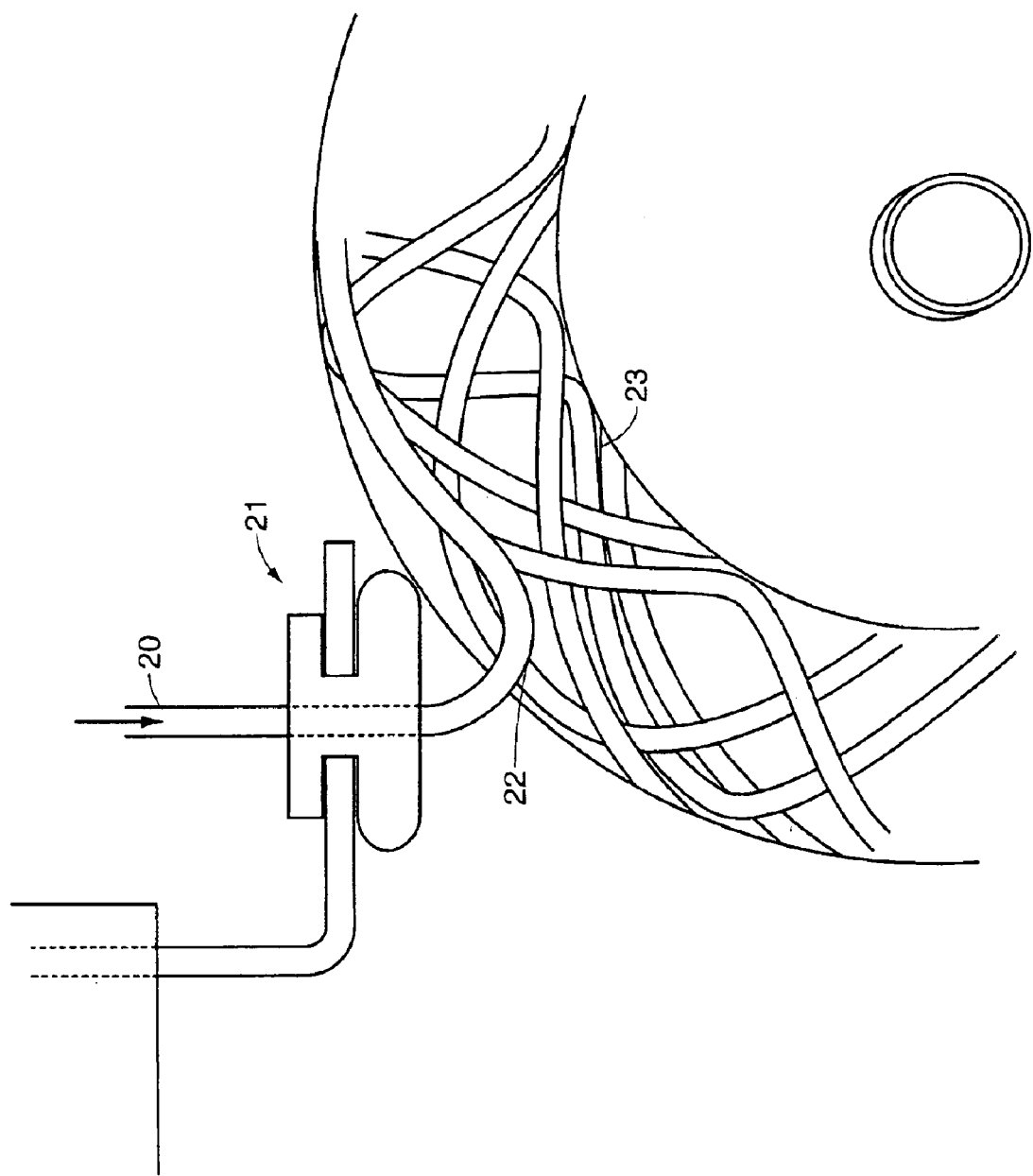
FIG. 2 is a schematic drawing of a bobbin of the coated monofilament tape as it is being wound onto the bobbin.

FIG. 2 illustrates in more detail the winding of coated monofilament tape, 20, as it passes through coating conditioning means, 21, creating a conditioned (pool) of coating suitable for tacking purposes, 22, on the bobbin, 23.

FIG. 3 illustrates monofilament tape, 30, with saliva soluble coatings, 31 and 32, having tack values between about 0.1 and about 0.5 grams.

It is understood, that for the purposes of the present invention, coating conditioning means such as heat tacking can be achieved by (1) using any one of a number of temperature conditioning devices such as a heating bar, a tube or box or low intensity warmed air zone such as produced by a heat lamp at fixed distance, all equipped to maintain a constant controllable temperature and, in the course of passage, pre-heat the monofilament tape and its coating to an optimum temperature, prior to (2) winding in combination with a directable source of energy to the bobbin itself during winding, as illustrated in FIGS. 1a and 1b.

Alternatively, a single, coating conditioning means can be used. For example, hot air heat tacking means, 6, as shown in FIGS. 1a and 1b, can be used during winding without temperature conditioning means, 4; provided that the underside of the tape, 2a through 2d, is properly heated and made "tacky" but not molten during winding by means, 6. Ideally, this is achieved by means of a heated ceramic eyelet as discussed below and shown in FIG. 1c and FIG. 2.

When coating conditioning means, 4, is used, it is maintained at a temperature such that in the "contact time" provided by the controlled line speed of the bobbin winding mechanism, it warms the coating and the tape to just below the softening temperature of the coating. In one embodiment, a short pass heating "bar" or other surface, at a surface temperature of between about 55° C. and 90° C. conducts sufficient energy to the tape coating without reaching the melt-temperature of the coating. Practically speaking, contact between the coated monofilament tape and coating conditioning means, 4, is at best, a "kiss". That is, the monofilament tape is traveling at between about 350 and 500 feet/second, and at these speeds, is barely touching the contact surface of coating conditioning means, 4, as shown in FIG. 1b. The net effect is that the coated tape is conditioned and made barely tacky by engaging coating conditioning means, 4, so that coated monofilament tapes, 2a through 2d, can be completely heat tacked during the winding process by the directed energy source, 6, just preceding the subsequent wraps of the tape on the bobbin under controlled or minimum tension.

The completion of the heat tacking step of applying directed energy, such as hot air to the bobbin during winding is designed to preferably heat the underside of the coated tape, thereby assuring that the final wraps of coated tape on the bobbin are secure, and that the shape of the bobbin is maintained without unwrapping of the tape strands, and/or of strands falling over the side of the bobbin. Such a hot air tacking source generally ranges in temperature from between about 50° and 90° C., while other energy forms are adjusted to momentarily raise the surface temperature of the "just about to be over-wrapped" segment of coated monofilament tape to a similar temperature.

To maintain suitable and essentially constant tension on the temperature conditioned coated tape and bobbin during winding, while avoiding bobbin deformation; the bobbin winding speed is constantly being varied as detailed in Tables 7 though 12 below. That is, at the outset, as the heated coated tape is introduced onto the bobbin core, the core is rotated at relatively higher rpm. This winding speed is then generally continuously reduced as the core is wound with numerous wraps of coated tape, eventually totaling from about 8 up to about 200 yds wound on the bobbin. That is, the winding speed continues to decelerate as the wraps on the bobbin increase and as the bobbin of coated monofilament tape increases in diameter. The directed hot air source envelopes and/or touches the bobbin during the entire procedure, such that the last piece of the coated monofilament tape comprising the last yard is tacked securely to the previous wrap on the bobbin.

A preferred means of achieving this substantially constant tension during winding is to use the Cezoma® bobbin winding machine model number CE 1487-8.0/10.2-91 fitted with a process control computer. The bobbin rotation at the beginning of the cycle (starting speed) is preferably in the range from between about 500 to 350 rpm spindle speed. To maintain suitable tension on the coated monofilament tape, this starting speed is then gradually reduced during the winding cycle by the process control computer by setting the rate of speed reduction such as to be gradually reduced throughout the wind cycle. It will be obvious to one skilled in the art that the desired shape of a speed reduction curve for a specific coated monofilament tape will be a function of the final thickness of the coating on the tape, as that determines the diameter of the bobbin being formed. See details in Tables 7 through 12 below, which describe additional examples of coated monofilament tape bobbins of the invention wound at various tensions.

EXAMPLE 1

An elastomeric monofilament tape 0.002 inches in thickness was coated with a saliva soluble coating as described in Example 77 in Table 5. The loading mechanism was adjusted to produce a coating load of approximately 53 mg/yd. This weight of coating ingredients produced a coating on both sides that was normally 0.001 inches thick (for an overall finished thickness of about 0.004 inches). When using a Cezoma® model number CE 1487 with code 36 set at 225 and Code 37 set at 965, an acceptable bobbin was formed. See also Table 6 below.

The Cezoma® was fitted with a temperature controlled heating bar having a shape such that approximately one inch of the surface touched the tape which passed by under light tension or pressure against the surface. For this example the temperature of the heating bar version of the Coating Conditioning means was maintained at 80° C. plus/minus 3° C.

The Cezoma® was also fitted with a hot air manifold which directed its energy to the underside of the bobbin such that the surface of the tape next to be overlaid in the wrapping rotation was exposed momentarily to a stream of air exiting the manifold at approximately 50° C.

Preferably, the ceramic eyelet on the traverse block on the winder is heated, thereby avoiding heating the entire bobbin during winding. By heating the ceramic eye, the coated monofilament tape is heated immediately prior to being laid onto the bobbin. This embodiment allows for producing wound bobbins of greater lengths without deformation attributed to excess heat energy. Details of this heated ceramic eyelet arrangement are illustrated in FIG. 2 of the drawings.

Under these conditions, substantially uniform bobbins containing 8 and 200 yds of product could be produced routinely at commercial speeds with no bobbin deformation. When placed in dispenser packages and stored, these bobbins can be dispensed without difficulty or loss of product integrity.

It is critical to this invention that both the rate of speed (rpm) change and the shape of the curve expressing said speed change be controlled according to the physical parameters of the coating on the tape being wound.

A series of coated elastomeric tapes as described in co-pending Provisional Patent Application Ser. No. 60/263,220, and as detailed in Table 5, were bobbin wound using the bobbin winding process of the present invention. The results of heating with single source of heat (or no heat) in a manner common to the industry are also described in Table 5 in the rows labeled "heat needed to wind" and "bobbin tack". However, when the method of heat tacking described herein was used, each formula could produce a nearly perfect bobbin with appropriately selected conditions for the elements of (1) coating conditioning, and (2) controlled tension.

Saliva soluble coatings for monofilament tapes to be bobbin wound according to the present invention are described in Table 5 below. In the Table, the term "Ultramulsion 10-2.5" is defined as an emulsion of polydimethylsiloxane (PDMS) at 2.5 million cs in a nonionic surfactant Poloxamer 407, where the PDMS is at 10% by weight of the total emulsion.

TABLE 5

| EXAMPLE | 60 | 61 | 62 | 63 | 64 | 65 | 66 | 67 | 68 | 69 | 70 | 71 | 72 | 73 | 74 | 75 | 76 | 77 |
|---|---|---|---|---|---|---|---|---|---|---|---|---|---|---|---|---|---|---|
| Ingredient | | | | | | | | | | | | | | | | | | |
| Ultramulsion 10-2.5* | 57.1 | 54.8 | 52.3 | 50.8 | 50.8 | 50.8 | 58.8 | 60.8 | | 60.1 | 55.1 | 51.1 | 60.1 | | 61.1 | 61.1 | 53.1 | 57.1 |
| POLOXAMER 407 | | | | | | | | | 60.1 | | | | | 60.1 | | | | |
| Emsorb 2726 | 12.5 | 7.5 | 12.5 | 9 | 5 | 3 | 3 | 0 | 3 | 3 | 3 | 3 | 3 | 3 | 4 | 3 | 3 | 3 |
| Stearyl Alcohol | 9.2 | 10.5 | 8 | 7 | 11 | 13 | 15 | 16 | 15 | 15 | 15 | 15 | 15 | 15 | 10 | 8 | 15 | 15 |
| Insoluable Saccharin | 1.8 | 1.8 | 1.8 | 1.8 | 1.8 | 1.8 | 1.8 | 1.8 | 1.8 | 1.8 | 1.8 | 1.8 | 1.8 | 1.8 | 1.8 | 1.8 | 1.8 | 1.8 |
| Propyl gallate | 0.1 | 0.1 | 0.1 | 0.1 | 0.1 | 0.1 | 0.1 | 0.1 | 0.1 | 0.1 | 0.1 | 0.1 | 0.1 | 0.1 | 0.1 | 0.1 | 0.1 | 0.1 |
| Spicemint Flavor | 4 | 4 | 4 | 4 | 4 | 4 | 4 | 4 | 5 | 5 | 5 | 5 | 5 | 5 | 5 | 5 | 5 | 5 |
| Vanilla Mint Flavor | 4 | 4 | 4 | 4 | 4 | 4 | 4 | 4 | 5 | 5 | 5 | 5 | 5 | 5 | 5 | 5 | 5 | 5 |
| tetrasodium-pyrophosphate | 8 | 14 | 14 | 10 | 10 | 10 | 10 | 10 | 10 | | 10 | 14 | 4 | | 6 | 6 | 10 | 6 |

TABLE 5-continued

| EXAMPLE | 60 | 61 | 62 | 63 | 64 | 65 | 66 | 67 | 68 | 69 | 70 | 71 | 72 | 73 | 74 | 75 | 76 | 77 |
|---|---|---|---|---|---|---|---|---|---|---|---|---|---|---|---|---|---|---|
| dicalcium phosphate | | | | | | | | | | 10 | | | 6 | 10 | | | | |
| Microcrystalline Wax ML 445 | | | 10 | 10 | 10 | 0 | 0 | 0 | 0 | | 5 | 5 | | 0 | 7 | 10 | 7 | 7 |
| Triclosan | 3.3 | 3.3 | 3.3 | 3.3 | 3.3 | 3.3 | 3.3 | 3.3 | | | | | | | | | | |
| Observation Need heat to wind | y | | n | y | y | n | Y | Y | y | y | y | y | y | y | y | y | y | y |
| Bobbin tack (1 = poor, 5 = good) | 1 | | 5 | 5 | 3 | 4 | | 4 | 3 | 2 | 4 | 4 | 3 | 3 | 4 | 3 | 4 | 4 |
| Flake resistance Feels sticky (1 = no, 5 = very) | | | 5 | 4 | 4 | 2 | 1 | | 2 | 2 | 3 | 3 | 3 | 1 | 4 | 3 | 4 | 4 |
| Load of two samples | 29/19 | na | na | 43/50 | 28/11 | 53/39 | 58/43 | 33/20 | 51/40 | 33 | 46/53 | 40/39 | 38/38 | 50/37 | 48 | 45 | 38/39 | 43/39 |

A series of examples illustrating the relationship between varying the control elements of this invention and bobbins wound is detailed in Table 6 below.

TABLE 6

| Example # | Table 1 Formula # @ mg/yd | Pre-heat Conditioning Bar in ° C. | Cezoma Starting Speed Code 36 | Cezoma Reduction Speed Code 37 | Directed Hot Air Temp in ° C. | Bobbin Quality |
|---|---|---|---|---|---|---|
| 78 | 18 @ 40 | 80 | 225 | 999 | 45 | excellent |
| 79 | 18 @ 60 | 85 | 225 | 985 | 55 | excellent |
| 80 | 17 @ 37 | 77 | 175 | 975 | 50 | excellent |
| 81 | 16 @ 50 | 90 | 125 | 965 | 53 | good-excel |
| 82 | 14 @ 55 | 85 | 75 | 905 | 60 | good |
| 83 | 15 @ 45 | none | 25 | 800 | 50 | Fair |
| 84 | 18 @ 50 | none | 0 | 500 | none | poor |

Similar bobbin winding results are obtained with coated PTFE and bicomponent dental tapes and other similarly coated polymeric tapes.

When either of the bobbin winding means of the present invention are deleted from the bobbin winding process, the resultant bobbins are of lesser quality and generally unsuitable for commercial use.

Another embodiment of the present invention is directed towards "dynamic cores" which are responsive to the compression forces created by extended exposure of the bobbins of coated monofilament tape to high heat and humidity, i.e., temperatures of 40° C. and above and relative humidity of 75% or greater.

Extended exposure of bobbins of coated monofilament tapes of the present invention to high temperatures and/or high relative humidity tends to either: (1) cause the molecules in the monofilament tape elastomer to re-orient causing the tape to contract as it becomes more elastomeric while applying increased compression pressure on the core, or (2) cause the saliva soluble coating to absorb more water and thereby increase the coating load while applying increased corresponding compression pressure onto the bobbin core.

Failure to provide relief from these compression forces results in either the coating oozing from between the winds of the bobbin onto the sides of the bobbin and/or the bobbin winds moving laterally causing a misshapen bobbin. In both instances, the bobbin generally does not dispense properly.

The dynamic cores of the present invention are responsive to these compression forces and tend to maintain the bobbin free from coating oozing and free from wind distortion when exposed to high temperature and high relative humidity conditions, thereby allowing the bobbin to dispense properly.

The dynamic cores of the present invention are manufactured from various substances including plastics and spring steel and are characterized by a variable diameter such that the core changes in diameter dimension in response to varying compression forces while maintaining a generally round dimension enabling it to rotate on the dispenser hub.

The compression forces on the core of coated monofilament tape loaded at 40 mg/m bobbin wound to 25 meters when stored at 40° C. and 75% humidity decreased the core diameter substantially after 90 days. After 90 days, when exposed to these conditions, the bobbin provided with a dynamic core remained substantially free from wind distortion and free from premature coating release and dispensed properly.

The corresponding bobbin wound at 50 meters and stored under comparable conditions produced a bobbin core with a substantially higher reduction in diameter after 90 days.

The compression tension on the core of the bobbins of the present invention are the product of the tension imposed on the coated monofilament tape as it winds onto the bobbin and as the bobbin is expanded from a single wind on its core to the multiple winds required to place 8, 10, 25, 50, 100 or 200 meters of coated monofilament tape onto the bobbin. As these winds of coated monofilament tape are built up on the bobbin the tension on latter winds of the coated monofilament tape is progressively reduced by reducing the revolutions per minute (rpm) the expanding bobbin core is being wound.

Thus, the tension placed on the 25$^{th}$ yard of coated monofilament tape wound onto a 25 yd bobbin is substantially less than the tension placed on the first yard of the tape wound onto the bobbin core. This reduction in tension on the tape as the bobbin is being wound is particularly critical to those coated monofilament tapes which may be placed under high temperature and/or high humidity conditions later on.

Set out below in Tables 7 through 12 are the results of bobbin winding a series of mono filament dental tapes of the invention coated with saliva soluble coatings as described in Table 5 at between about 30 mg/yd and about 60 mg/yd. These bobbins were wound using a Cezoma®, Model No. CE 1487 with Code 36 set at: 25, 75, 125, 175, 225 and 255, respectively, and Code 37 having start and finish RPM as reported. The Tack Values for some of these bobbins are detailed in Table 14 below.

TABLE 7

Code 36 @ 25

| Code 37 | RPM Start | RPM Finish |
|---|---|---|
| 999 | 411 | 382 |
| 985 | 411 | 382 |
| 965 | 411 | 382 |
| 955 | 411 | 382 |
| 935 | 411 | 382 |
| 905 | 411 | 382 |
| 800 | 411 | 382 |
| 700 | 411 | 382 |
| 600 | 411 | 382 |
| 500 | 411 | 389 |
| 400 | 411 | 389 |
| 300 | 411 | 389 |
| 200 | 411 | 389 |
| 100 | 413 | 395 |
| 0 | 488 | 488 |

TABLE 8

Code 36 @ 75

| Code 37 | RPM Start | RPM Finish |
|---|---|---|
| 999 | 494 | 382 |
| 985 | 494 | 382 |
| 965 | 494 | 382 |
| 955 | 494 | 384 |
| 935 | 494 | 419 |
| 905 | 494 | 444 |
| 800 | 494 | 470 |
| 700 | 494 | 455 |
| 600 | 494 | 470 |
| 500 | 490 | 472 |
| 400 | 499 | 485 |
| 300 | 498 | 481 |
| 200 | 499 | 468 |
| 100 | 499 | 485 |
| 0 | 494 | 487 |

TABLE 9

Code 36 @ 125

| Code 37 | RPM Start | RPM Finish |
|---|---|---|
| 999 | 457 | 378 |
| 985 | 554 | 384 |
| 965 | 556 | 382 |
| 955 | 565 | 382 |
| 935 | 577 | 420 |
| 905 | 567 | 472 |
| 800 | 577 | 531 |
| 700 | 575 | 547 |
| 600 | 573 | 549 |
| 500 | 573 | 553 |
| 400 | 573 | 556 |
| 300 | 573 | 556 |
| 200 | 573 | 558 |
| 100 | 573 | 569 |
| 0 | 573 | 572 |

TABLE 10

Code 36 @ 175

| Code 37 | RPM Start | RPM Finish |
|---|---|---|
| 999 | 514 | 384 |
| 985 | 635 | 378 |
| 965 | 641 | 542 |
| 955 | 644 | 453 |
| 935 | 644 | 520 |
| 905 | 646 | 556 |
| 800 | 646 | 608 |
| 700 | 650 | 624 |
| 600 | 650 | 632 |
| 500 | 650 | 633 |
| 400 | 650 | 632 |
| 300 | 650 | 637 |
| 200 | 650 | 630 |
| 100 | 650 | 641 |
| 0 | 650 | 648 |

TABLE 11

Code 36 @ 225

| Code 37 | RPM Start | RPM Finish |
|---|---|---|
| 999 | 600 | 380 |
| 985 | 709 | 481 |
| 965 | 716 | 496 |
| 955 | 716 | 554 |
| 935 | 720 | 575 |
| 905 | 722 | 632 |
| 800 | 720 | 689 |
| 700 | 725 | 703 |
| 600 | 723 | 707 |
| 500 | 727 | 714 |
| 400 | 734 | 720 |
| 300 | 727 | 714 |
| 200 | 725 | 716 |
| 100 | 725 | 718 |
| 0 | 727 | 727 |

TABLE 12

Code 36 @ 255

| Code 37 | RPM Start | RPM Finish |
|---|---|---|
| 999 | 655 | 389 |
| 985 | 755 | 551 |
| 965 | 747 | 553 |
| 955 | 760 | 611 |
| 935 | 766 | 648 |

TABLE 12-continued

Code 36 @ 255

| Code 37 | RPM Start | RPM Finish |
|---|---|---|
| 905 | 766 | 701 |
| 800 | 769 | 736 |
| 700 | 771 | 718 |
| 600 | 771 | 756 |
| 500 | 773 | 758 |
| 400 | 773 | 760 |
| 300 | 771 | 762 |
| 200 | 773 | 762 |
| 100 | 773 | 767 |
| 0 | 771 | 767 |

For the purposes of the present invention, Tack Values for the bobbins of coated monofilament dental tape are determined by measuring the amount of free-hanging tape in grams, suspended from the bobbins, needed to overcome the tack of the wound tape on the bobbins, wherein once this tack value is attained, the bobbin will continue to unwind, being driven by the weight of the tape suspended from the bobbin.

The tack values for commercial products were determined by adding weight to the unwound, suspended product until the tack of the bobbin was overcome and the bobbin would continue to unwind, driven by the suspended product/weight combination.

One of the surprising and distinguishing features of the coated monofilament dental floss bobbins of the present invention are the Bobbin Tack Values for the bobbins of the present invention compared to the Bobbin Tack Values for various commercial dental tapes and flosses.

Figure 4:
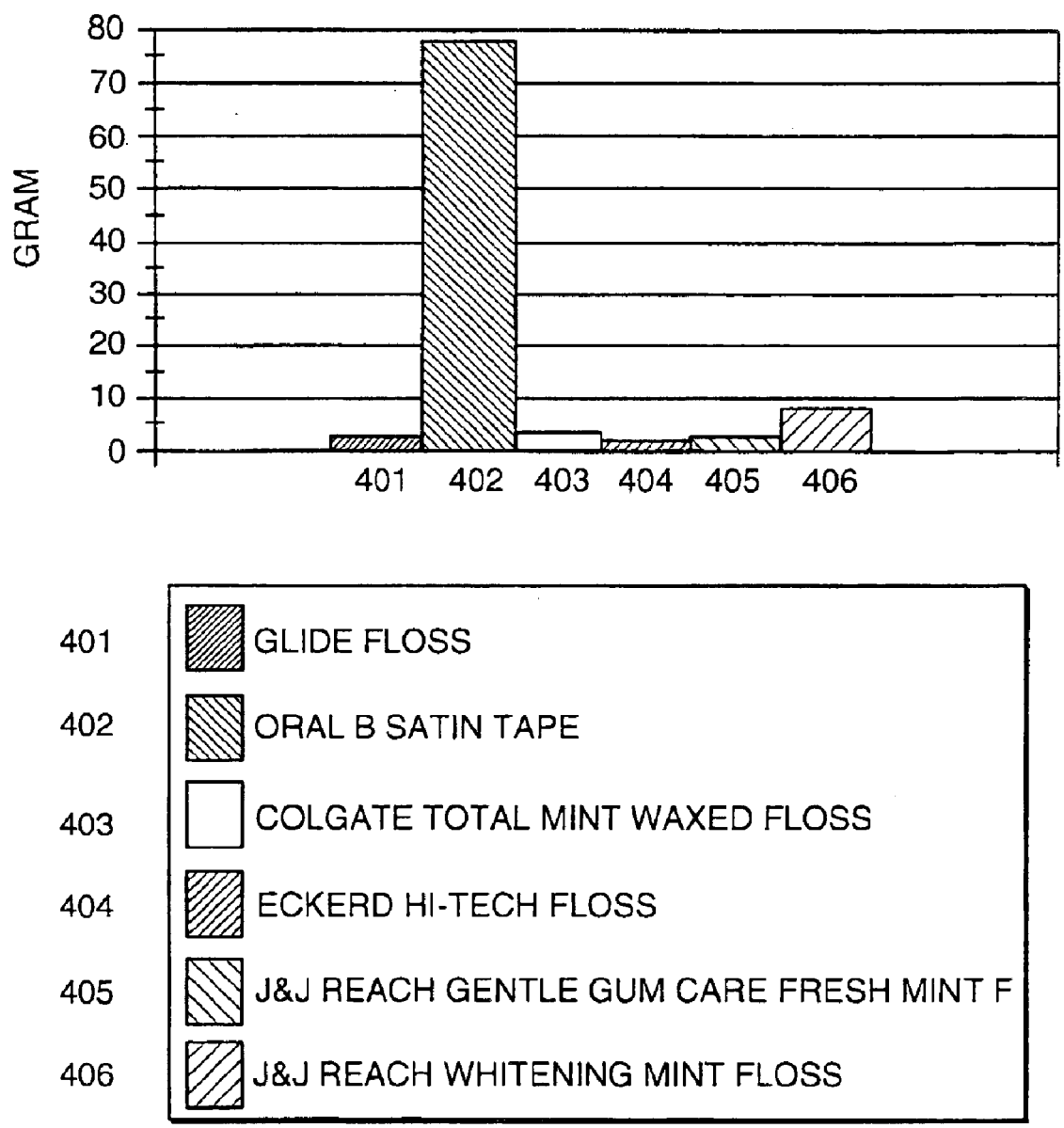
FIGS. 4 through 10 are bar charts detailing Tack Values for bobbins of various commercial interproximal devices and for bobbins of the present invention.

The Bobbin Tack Values for various commercial interproximal devices are summarized in FIG. 4, a bar chart setting out these relative Bobbin Tack Values.

Figure 5:
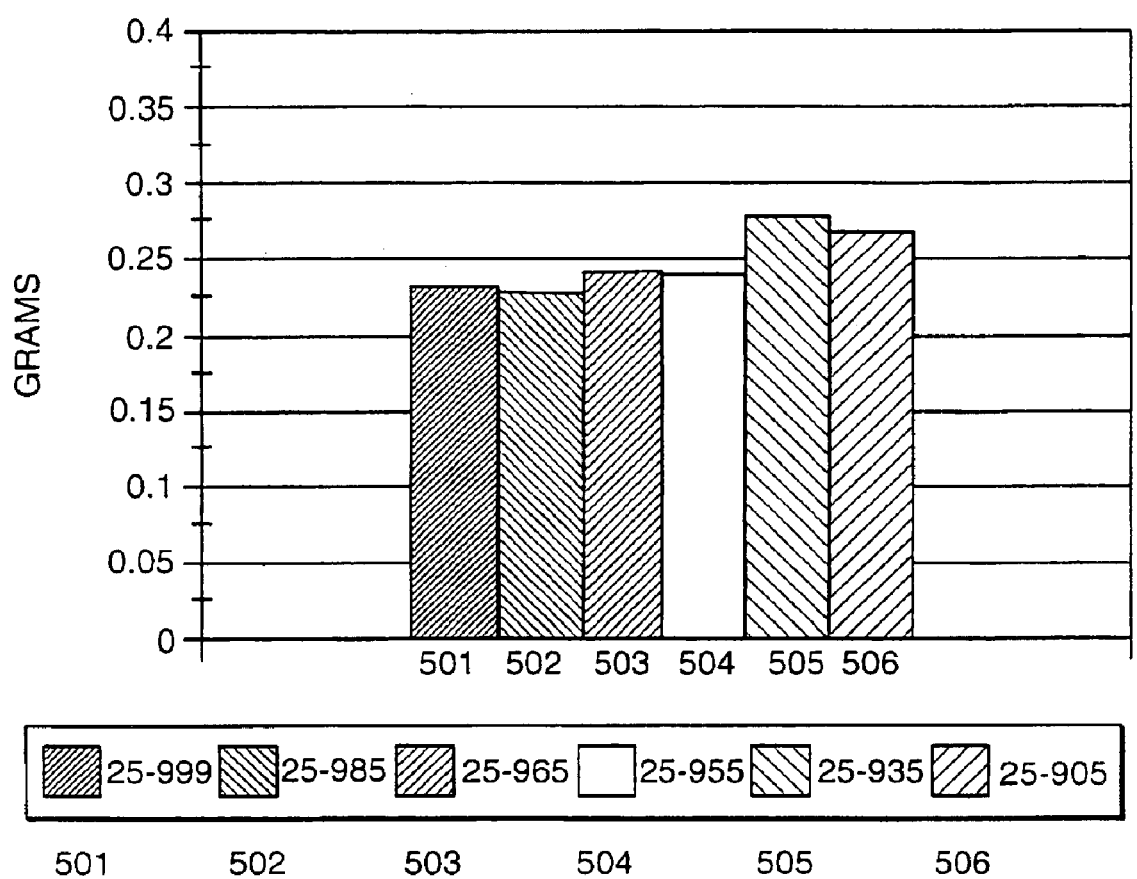
Figure 6:
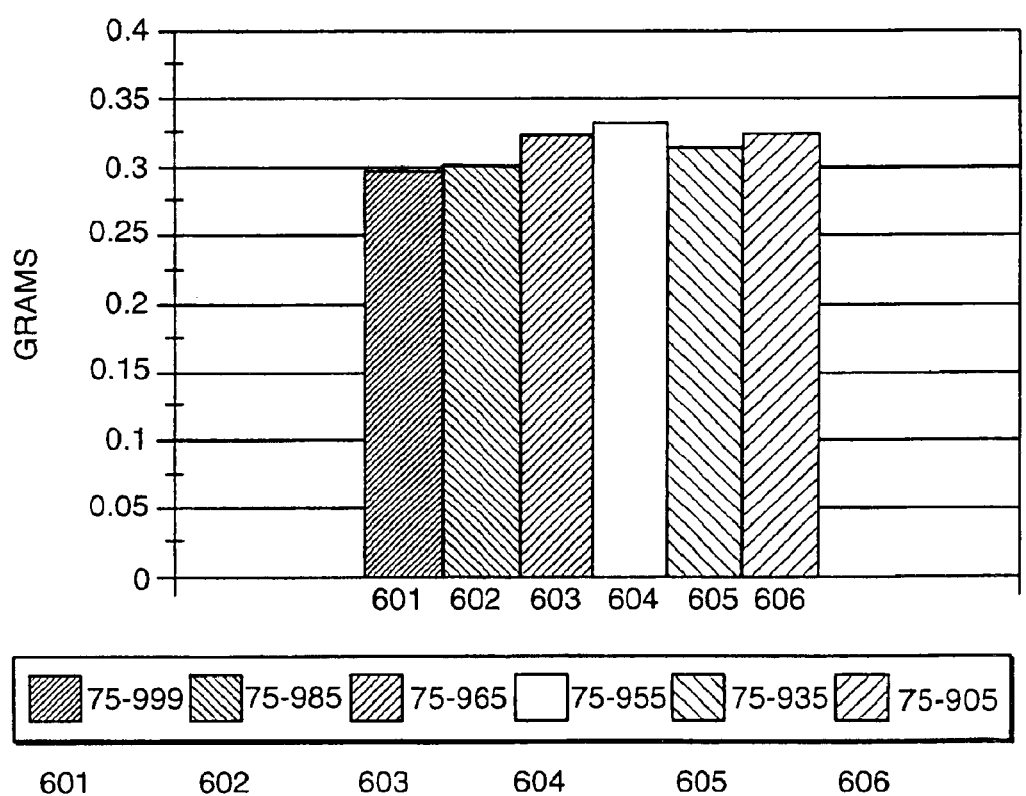
Figure 7:
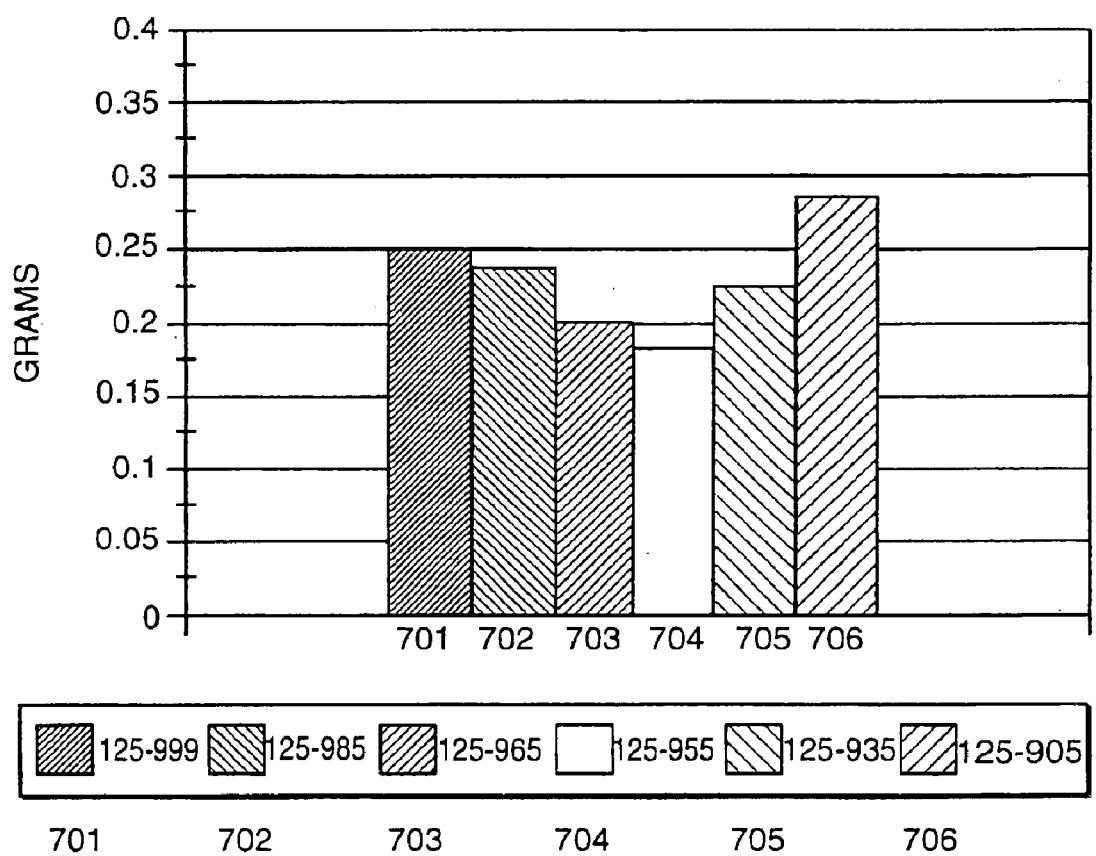
Figure 8:
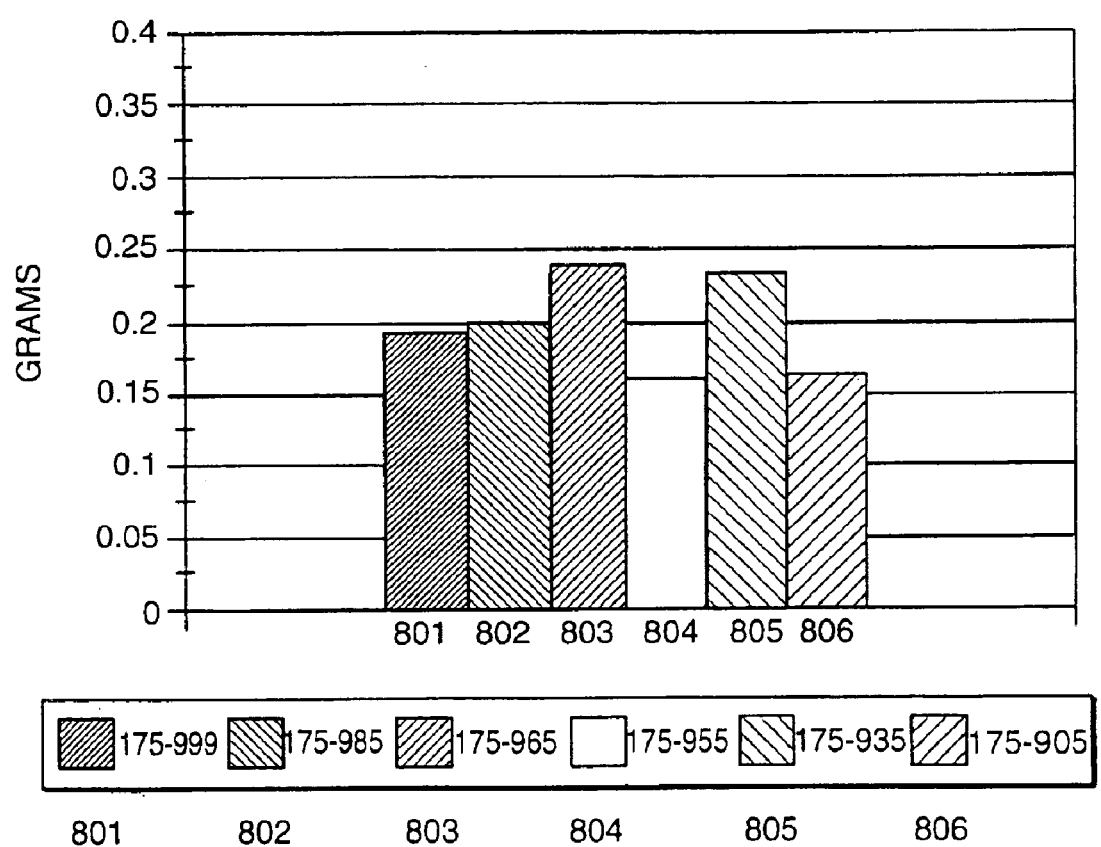
Figure 9:
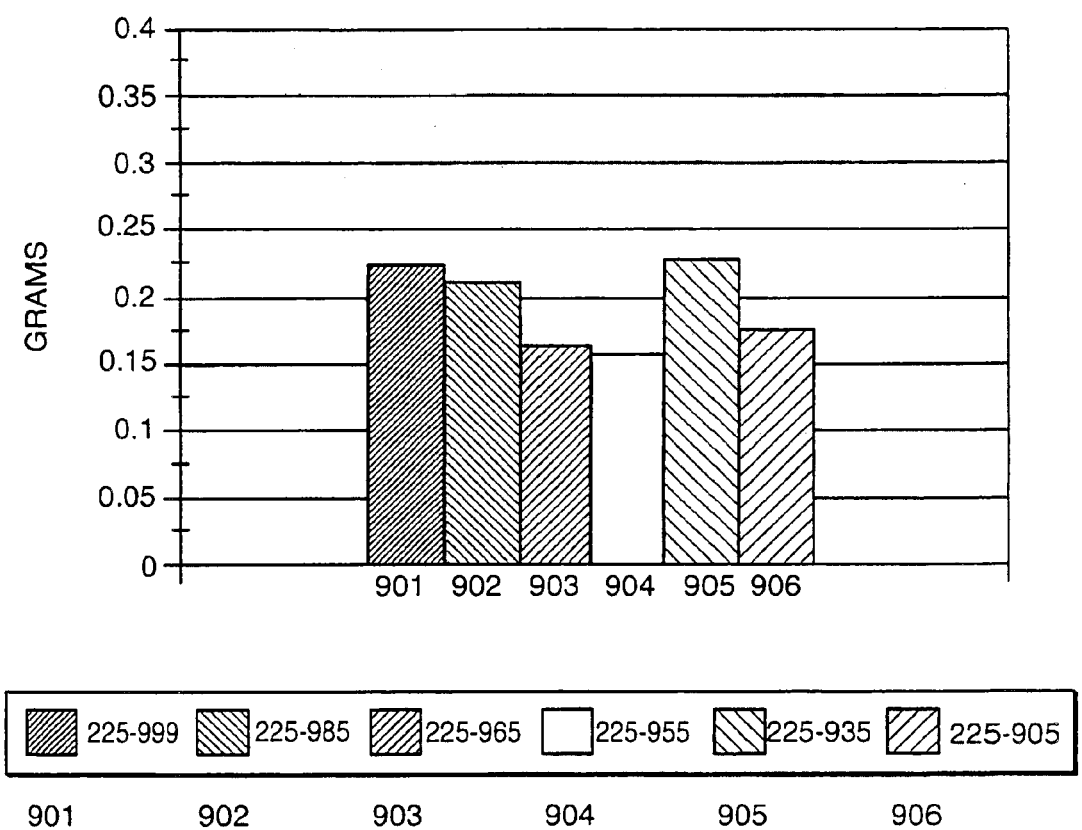
Figure 10:
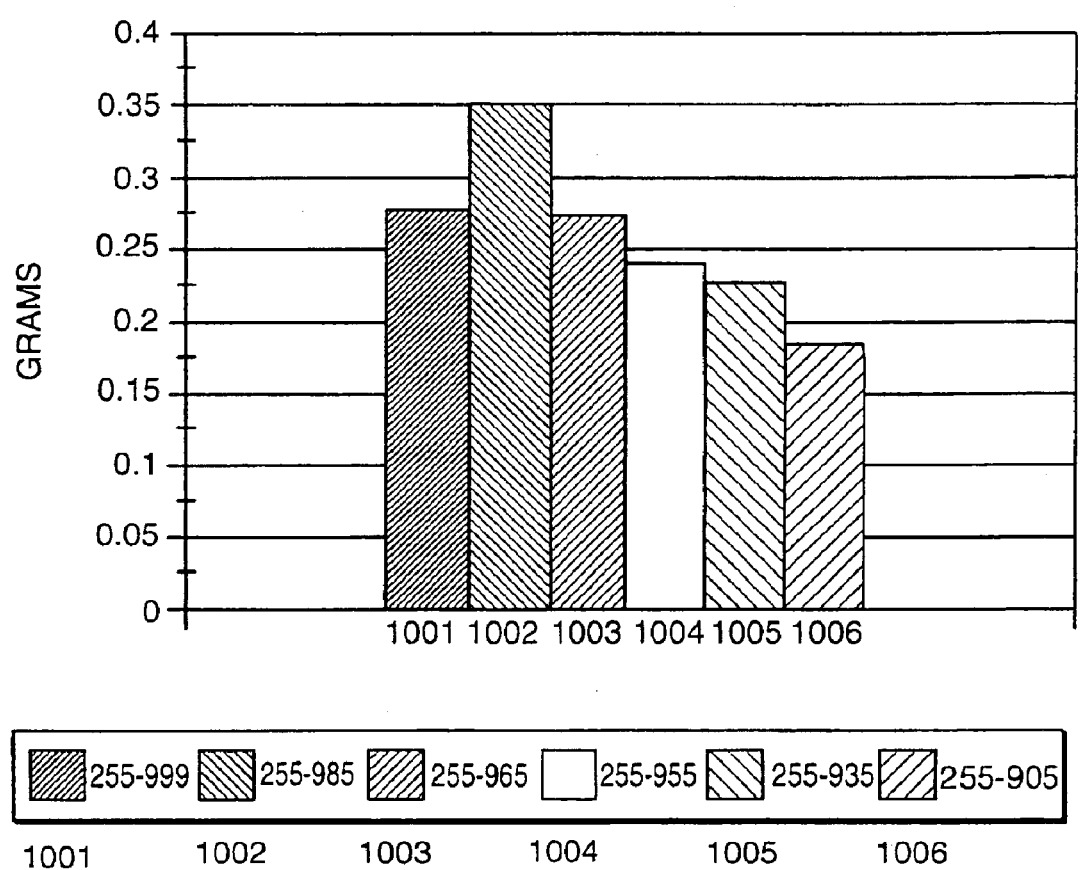

The Bobbin Tack Values for the various bobbins of the present invention as described in Tables 7 through 12 are summarized in Table 14 and FIG. 5.

Clearly, the Bobbin Tack Values for the bobbins of the present invention are dramatically lower than current commercial products.

TABLE 13

Floss Bobbin Tack Value in Grams

| | |
|---|---|
| Glide ® Floss | 2.2258 |
| Oral-B Satin Tape ® | 78.0629 |
| Colgate Total ® Mint Waxed Floss | 3.2872 |
| Eckerd Hi-Tech Floss | 2.1775 |
| J&J REACH ® Gentle Gum Care Fresh Mint Floss | 2.5953 |
| J&J REACH ® Whitening Mint Floss | 8.2387 |

TABLE 14

Coated Monofilament Tape
Bobbin winder settings are as follows: Code 36 (Winding Speed) = 25, 75, 125, 175, 225, 255; Code 37 (Reduction Speed) = 999, 985, 965, 955, 935, 905; Air Heat Temperature = 76.3° C.; Eyelet Temperature = 60.4° C.

| BOBBIN | TACK VALUE in grams |
|---|---|
| 255-999 | 0.2768 |
| 225-999 | 0.2233 |
| 175-999 | 0.1906 |
| 125-999 | 0.2505 |
| 75-999 | 0.2984 |
| 25-999 | 0.2302 |
| 255-985 | 0.3516 |
| 225-985 | 0.2130 |
| 175-985 | 0.1985 |
| 125-985 | 0.2365 |
| 75-985 | 0.3015 |
| 25-985 | 0.2278 |
| 255-965 | 0.2759 |
| 225-965 | 0.1632 |
| 175-965 | 0.2367 |
| 125-965 | 0.1977 |
| 75-965 | 0.3230 |
| 25-965 | 0.2414 |
| 255-955 | 0.2411 |
| 225-955 | 0.1570 |
| 175-955 | 0.1591 |
| 125-955 | 0.1819 |
| 75-955 | 0.3320 |
| 25-955 | 0.2404 |
| 225-935 | 0.2290 |
| 225-935 | 0.2279 |
| 175-935 | 0.2298 |
| 125-935 | 0.2243 |
| 75-935 | 0.3146 |
| 25-935 | 0.2778 |
| 255-905 | 0.1826 |
| 225-905 | 0.1770 |
| 175-905 | 0.1617 |
| 125-905 | 0.2856 |
| 75-905 | 0.3251 |
| 25-905 | 0.2689 |

The present invention has been described in detail, including the preferred embodiments thereof. However, it will be appreciated that those skilled in the art, upon consideration of the present disclosure, may make modifications and/or improvements on this invention and still be within the scope and spirit of this invention as set forth in the following claims.

What is claimed is:

1. In a process for bobbin winding coated monofilament dental tapes,
wherein the coating comprises two or more coating materials, and wherein the coating amount ranges from between about 20% by weight and about 120% by weight of said tape; the improvement comprising:
employing a coating conditioning means in combination with a decelerating winding speed tape tension control means to maintain essentially constant tension on the coated monofilament tape as it is bobbin wound;
wherein the conditioning means comprises a controllable heat surface for contacting and warming the coating and the tape to a temperature just below the softening temperature of the coating, prior to bobbin winding.

2. The process of claim 1, wherein the bobbin after winding has a tack value between about 0.1 and about 0.5 grams.

3. The process according to claim 1, wherein said coated monofilament tape is selected from the group consisting of polytetra-fluoroethylene, elastomer, bicomponent and homopolymer tapes.

4. The process according to claim 1, wherein the coating conditioning means further comprises a source of directed energy selected from the group consisting of radiant heat, lasers, radio frequency and combinations thereof targeted onto the bobbin during winding.

5. In a process for bobbin winding coated monofilament dental tapes, wherein the coating comprises two or more coating materials, and wherein the coating ranges from between about 20% by weight and about 120% by weight of said tape; the improvement comprising:

employing a coating conditioning means in combination with a decelerating winding speed tape tension control means to maintain essentially constant tension on the coated monofilament tape as it is bobbin wound;

wherein the coating conditioning means comprises a controllable heating zone through which said coated monofilament tape passes prior to bobbin winding, to warm the coating and the tape to a temperature just below the softening temperature of the coating.

6. The process of claim 5, wherein the bobbin after winding has a tack value between about 0.1 and about 0.5 grams.

7. The process according to claim 5, wherein said coated monofilament tape is selected from the group consisting of polytetra-fluoroethylene, elastomer, bicomponent and homopolymer tapes.

8. The process according to claim 5, wherein the coating conditioning means further comprises a source of directed energy selected from the group consisting of radiant heat, lasers, radio frequency and combinations thereof targeted onto the bobbin during winding.

* * * * *